US00PP21478P2

(12) United States Plant Patent
van den Hoogen

(10) Patent No.: US PP21,478 P2
(45) Date of Patent: Nov. 16, 2010

(54) ***VERONICA* PLANT NAMED 'ALLLOVE'**
(50) Latin Name: *Veronica longifolia*
Varietal Denomination: Alllove

(75) Inventor: Wilhelmus T. J. van den Hoogen, Cuijk (NL)

(73) Assignees: All Plants Holding B.V., Cuijk (NL); Stuart Scott, Nakuru (KE)

( * ) Notice: Subject to any disclaimer, the term of this patent is extended or adjusted under 35 U.S.C. 154(b) by 0 days.

(21) Appl. No.: 12/456,337

(22) Filed: Jun. 15, 2009

(51) Int. Cl.
*A01H 5/00* (2006.01)

(52) U.S. Cl. ..... Plt./251
(58) Field of Classification Search ..... Plt./251

See application file for complete search history.

*Primary Examiner*—Annette H Para
(74) *Attorney, Agent, or Firm*—C. A. Whealy

(57) ABSTRACT

A new and distinct cultivar of *Veronica* plant named 'Alllove', characterized by its upright plant habit; freely flowering habit; compact and dense inflorescences with numerous intense red purple-colored flowers; and long flowering period.

3 Drawing Sheets

Botanical designation: *Veronica longifolia.*

Cultivar denomination: 'ALLLOVE'.

BACKGROUND OF THE INVENTION

The present invention relates to a new and distinct cultivar of *Veronica* plant, botanically known as *Veronica longifolia* and hereinafter referred to by the name 'Alllove'.

The new *Veronica* plant is a product of a planned breeding program conducted by the Inventor in Cuijk, The Netherlands. The objective of the breeding program is to create new cut flower *Veronica* cultivars with attractive flower coloration.

The new *Veronica* plant originated from an open-pollination during the summer of 2002 of a proprietary selection of *Veronica longifolia* identified as code number VZ033CCBP1, not patented, as the female, or seed, parent with an unknown selection of *Veronica longifolia* as the male, or pollen, parent. The new *Veronica* was discovered and selected by the Inventor as a single flowering plant from within the progeny of the stated open-pollination grown in a controlled environment in Cuijk, The Netherlands in June, 2004.

Asexual reproduction of the new *Veronica* plant by vegetative cuttings in a controlled environment in Cuijk, The Netherlands, since July, 2004, has shown that the unique features of this new *Veronica* plant are stable and reproduced true to type in successive generations.

SUMMARY OF THE INVENTION

Plants of the new *Veronica* have not been observed under all possible environmental conditions. The phenotype may vary somewhat with variations in environment such as temperature and light intensity without, however, any variance in genotype.

The following traits have been repeatedly observed and are determined to be the unique characteristics of 'Alllove'. These characteristics in combination distinguish 'Alllove' as a new and distinct cultivar of *Veronica:*

1. Upright plant habit.
2. Freely flowering habit.

3. Compact and dense inflorescences with numerous intense red purple-colored flowers.
4. Long flowering period.

Plants of the new *Veronica* differ from plants of the female parent selection primarily in flower color as plants of the female parent selection have soft pink-colored flowers.

Plants of the new *Veronica* can be compared to plants of *Veronica spicata* 'Rotfuchs', not patented. In side-by-side comparisons conducted in Cuijk, The Netherlands, plants of the new *Veronica* differed from plants of 'Rotfuchs' in the following characteristics:

1. Plants of the new *Veronica* had broader leaves than plants of 'Rotfuchs'.
2. Plants of the new *Veronica* had wider and denser inflorescences than plants of 'Rotfuchs'.

BRIEF DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new *Veronica* plant.

The photograph on the first sheet comprises a side perspective view of a typical flowering plant of 'Alllove' grown in a container.

The photograph on the second sheet is a close-up view of a typical inflorescence of 'Alllove'.

The photograph on the third sheet is a close-up view of a typical leaf of 'Alllove'.

DETAILED BOTANICAL DESCRIPTION

Plants used for the aforementioned photographs and following description were grown under conditions which closely approximate commercial production conditions during the summer in an outdoor nursery in Cuijk, The Netherlands. During the production of the plants, day temperatures ranged from 12° C. to 32° C. and night temperatures ranged from 4° C. to averaged 16° C. Plants were two years old when the photographs and the description were taken. In the following description, color references are made to The Royal Horticultural Society Colour Chart, 2001 Edition, except where general terms of ordinary dictionary significance are used.

Botanical classification: *Veronica longifolia* 'Alllove'.

Parentage:

*Female, or seed, parent.*—Proprietary selection of *Veronica longifolia* identified as code number VZ033CCBP1, not patented.

*Male, or pollen, parent.*—Unknown selection of *Veronica longifolia,* not patented.

Propagation:

*Type cutting.*—Vegetative cuttings.

*Time to initiate roots.*—About 10 to 14 days at 12° C. to 30° C.

*Time to produce a rooted young plant.*—About 24 to 32 days at 12° C. to 30° C.

*Root description.*—Fine, fleshy; white in color.

*Rooting habit.*—Freely branching; dense.

Plant description:

*Plant type.*—Herbaceous perennial.

*Plant and growth habit.*—Upright inverted triangle; freely branching habit with about seven main stems each with about eight lateral branches; moderately vigorous growth habit.

*Plant height.*—About 39.8 cm.

*Plant width.*—About 37.7 cm.

*Lateral branch description.*—Length: About 12.1 cm. Diameter: About 3 mm. Internode length: About 4.2 cm. Strength: Strong. Texture: Densely pubescent. Color: Close to 143B.

Foliage description:

*Arrangement.*—Opposite, simple.

*Length.*—About 6.3 cm.

*Width.*—About 3.6 cm.

*Shape.*—Ovate.

*Apex.*—Broadly acute.

*Base.*—Cordate.

*Margin.*—Serrate.

*Texture, upper and lower surfaces.*—Sparsely pubescent.

*Venation pattern.*—Pinnate.

*Color.*—Developing leaves, upper surface: Between 141A and 143A. Developing leaves, lower surface: Close to 143A to 143B. Fully expanded leaves, upper surface: Darker than between 137A and 147A; venation, close to 144B. Fully expanded leaves, lower surface: Close to 137B and 137C; venation, close to 144B.

*Petiole length.*—About 1.7 cm.

*Petiole diameter.*—About 2 mm by 3 mm.

*Petiole texture, upper and lower surfaces.*—Sparsely pubescent.

*Petiole color, upper and lower surfaces.*—Close to 144B.

Flower description:

*Flower arrangement and shape.*—Single campanulate flowers arranged on terminal racemes; racemes compact and dense; flowers face mostly outwardly.

*Flowering habit.*—Freely flowering, about 400 flowers per inflorescence.

*Fragrance.*—Not detected.

*Natural flowering season.*—Flowering continuous from July to late September in The Netherlands.

*Flower longevity on the plant.*—About one week; flowers persistent.

*Flower buds.*—Length: About 6 mm. Diameter: About 2 mm. Shape: Narrowly ovate. Color: Close to N66A to N66B.

*Inflorescence height.*—About 9.7 cm.

*Inflorescence diameter.*—About 2.4 cm.

*Flower diameter.*—About 7 mm.

*Flower height* (*depth*).—About 1 cm.

*Petals.*—Arrangement: Four, fused about 42.5% from the base. Length: About 7 mm. Width: About 2.5 mm to 3 mm. Shape: Oblanceolate. Apex: Broadly acute. Margin: Entire. Texture, upper and lower surfaces: Smooth, glabrous. Color: When opening and fully opened, upper surface: Between 61C and N66B. When opening and fully opened, lower surface: Between 61C and N66B.

*Calyx.*—Shape: Four sepals fused into a tube; ovate to narrowly ovate; apices, acute; margin, entire. Length: About 2 mm to 3 mm. Width: About 1 mm. Texture, upper and lower surfaces: Smooth, glabrous. Color, immature and mature, upper surface: Close to 143A. Color, immature and mature, lower surface: Close to 143C.

*Peduncles.*—Strength: Strong. Length: About 9.3 cm. Diameter: About 3 mm. Aspect: Mostly upright. Texture: Smooth, glabrous. Color: Close to 143C.

*Pedicels.*—Strength: Strong. Length: About 1 mm. Diameter: About 0.5 mm. Aspect: About 60° from vertical. Texture: Smooth, glabrous. Color: Close to 143B to 143C.

*Reproductive organs.*—Stamens: Quantity per flower: Two. Filament length: About 7 mm. Filament color: Close to 70B. Anther shape: Elliptic. Anther length: About 2 mm. Anther color: Close to N77B. Pollen amount: Scarce. Pollen color: Close to 159D. Pistils: Quantity per flower: One. Pistil length: About 6 mm. Stigma shape: Clavate. Stigma color: Close to N79C. Style length: About 5.5 mm. Style color: Close to N78B. Ovary color: Close to 144B to 144C.

*Seeds/fruits.*—Seed and fruit development have not been observed on plants of the new *Veronica.*

Disease/pest resistance: Plants of the new *Veronica* have not been noted to be resistant to pathogens and pests common to *Veronica.*

Garden performance: Plants of the new *Veronica* have exhibited good tolerance to rain and wind and have been observed to tolerate temperatures ranging from −25° C. to 35° C.

It is claimed:

1. A new and distinct *Veronica* plant named 'Alllove' as illustrated and described.

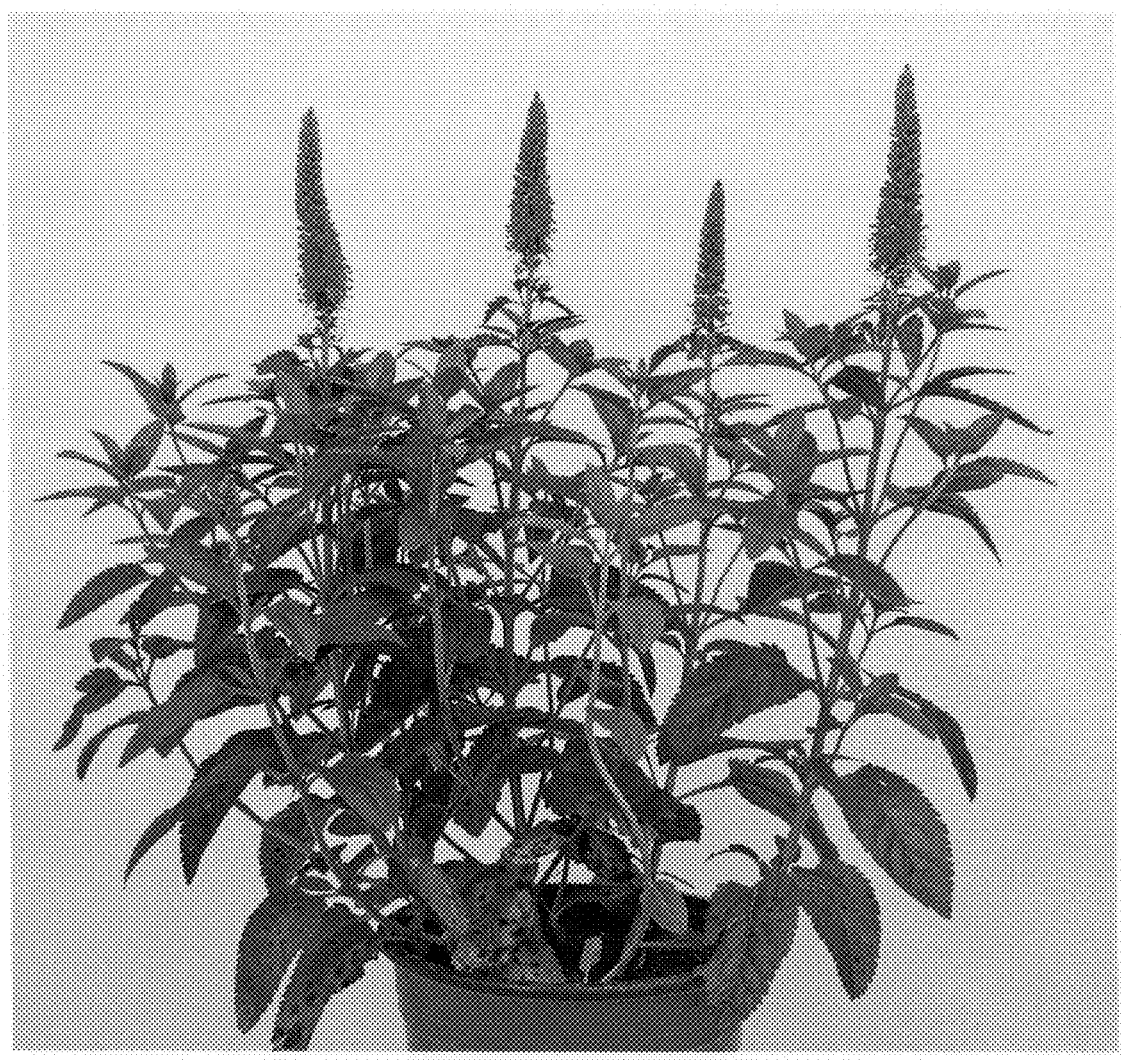

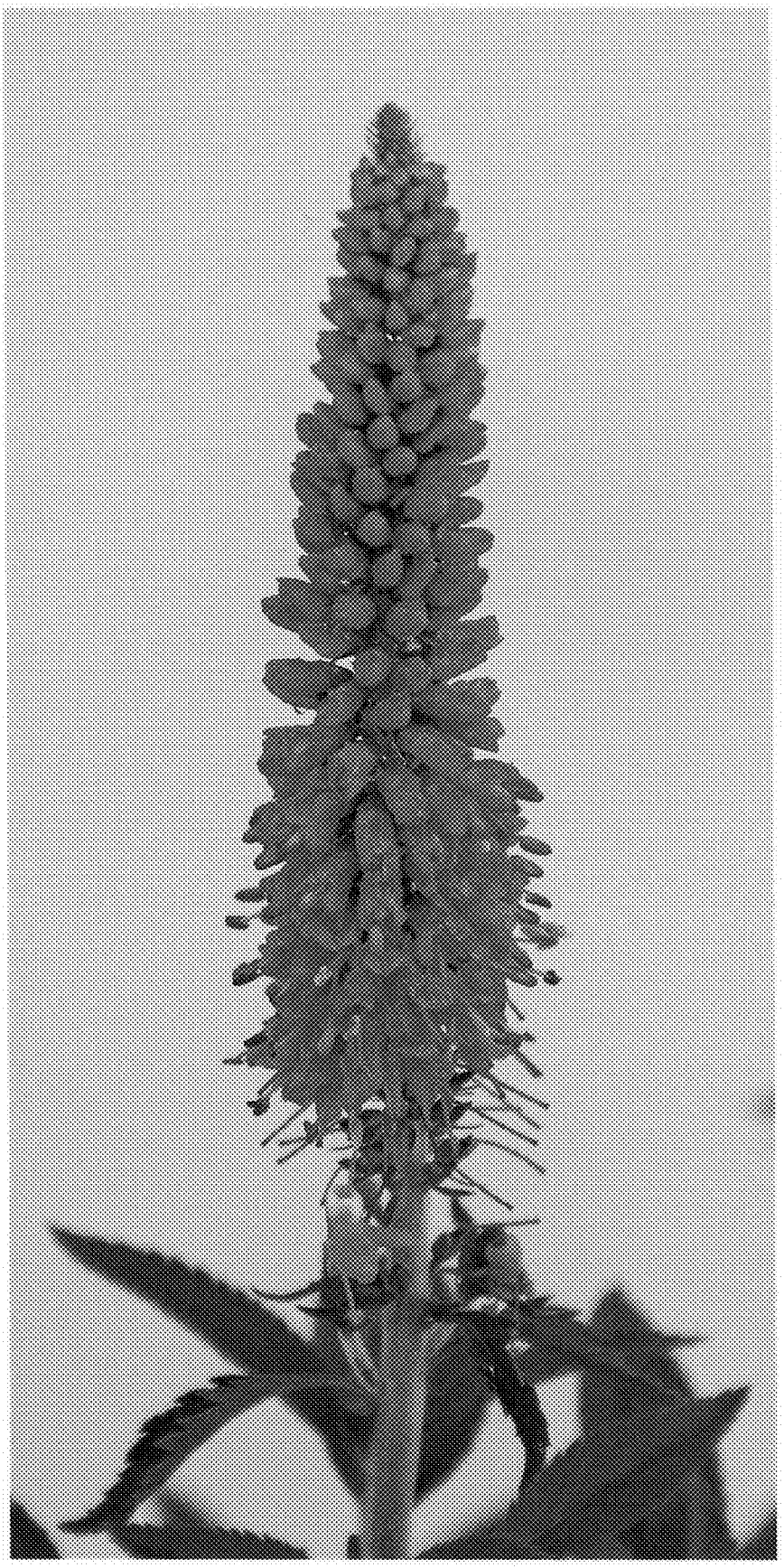

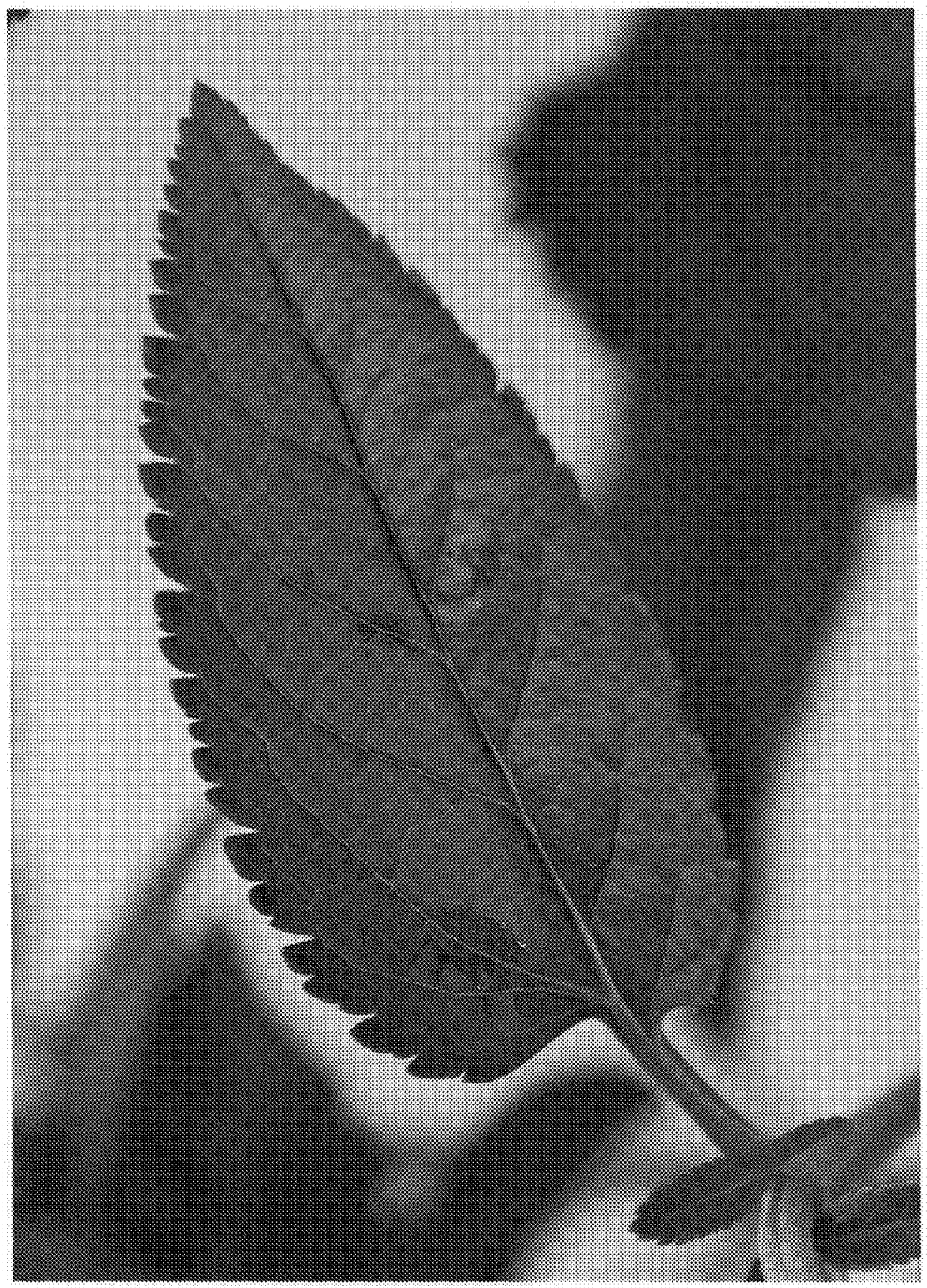

* * * * *